United States Patent [19]

Newbower

[11] Patent Number: 4,817,624
[45] Date of Patent: Apr. 4, 1989

[54] MINI-BOLUS TECHNIQUE FOR THERMODILUTION CARDIAC OUTPUT MEASUREMENTS

[75] Inventor: Ronald S. Newbower, Acton, Mass.

[73] Assignee: The General Hospital Corporation, Boston, Mass.

[21] Appl. No.: 811,684

[22] Filed: Dec. 20, 1985

[51] Int. Cl.$^4$ .............................................. A61B 5/02
[52] U.S. Cl. ........................................ 128/692; 128/713
[58] Field of Search ................ 128/4, 6, 691, 692, 128/713, 736; 604/53, 171, 173, 264, 280, 284

[56] References Cited

U.S. PATENT DOCUMENTS

| | | | |
|---|---|---|---|
| 2,460,473 | 2/1949 | Smith | 128/349 |
| 3,330,269 | 7/1967 | Pieper | 128/2.05 |
| 3,487,826 | 1/1970 | Barefoot | 128/2.05 F |
| 3,545,428 | 12/1970 | Webster | 128/2.05 |
| 3,583,404 | 6/1971 | McWhorter | 128/349 |
| 3,593,713 | 7/1971 | Bogoff | 604/280 |
| 3,595,079 | 7/1971 | Grahn | 73/294 |
| 3,734,083 | 5/1973 | Kolin | 128/2.05 F |
| 3,798,967 | 3/1974 | Gieles et al. | 128/2.5 F |
| 3,805,787 | 4/1974 | Banko | 128/276 |
| 3,838,683 | 10/1974 | Kolin | 128/2.05 F |
| 3,896,373 | 7/1975 | Zelby | 128/2.05 |
| 3,902,492 | 9/1975 | Greenhalgh | 128/241 |
| 3,911,742 | 10/1975 | Kolin | 128/2.05 F |
| 4,099,528 | 7/1978 | Sorenson et al. | 128/214.4 |
| 4,144,884 | 3/1979 | Tersteegen et al. | 128/214.4 |
| 4,153,048 | 5/1979 | Magrini | 128/692 |
| 4,175,566 | 11/1979 | Millar | 128/692 |
| 4,178,936 | 12/1979 | Newcomb | 128/349 B |
| 4,212,298 | 7/1980 | Gezari | 128/215 |
| 4,217,895 | 8/1980 | Sagae et al. | 128/214.4 |
| 4,217,910 | 8/1980 | Khahil | 128/670 |
| 4,230,126 | 10/1980 | Elings | 128/671 |
| 4,236,523 | 12/1980 | Gruenwald | 128/419 PT |
| 4,240,441 | 12/1980 | Khahil | 128/692 |
| 4,270,535 | 6/1981 | Bogue et al. | 128/214.4 |
| 4,281,665 | 8/1981 | Gezari | 128/713 |
| 4,299,217 | 11/1981 | Sagae et al. | 125/214.4 |
| 4,329,983 | 5/1982 | Lieber et al. | 604/280 |
| 4,403,615 | 9/1983 | Hoehner | 128/692 |
| 4,403,983 | 9/1983 | Edelman et al. | 604/43 |
| 4,406,656 | 9/1983 | Hattler et al. | 604/280 |
| 4,423,725 | 1/1984 | Baran et al. | 128/207.15 |
| 4,451,252 | 5/1984 | Martin | 604/43 |
| 4,468,216 | 8/1984 | Mato | 604/43 |
| 4,476,877 | 10/1984 | Barker | 128/736 |
| 4,484,585 | 11/1984 | Baier | 604/280 |
| 4,569,335 | 2/1986 | Tsuno | 128/6 |
| 4,589,404 | 5/1986 | Barath et al. | 128/6 |
| 4,601,706 | 7/1986 | Aillon | 604/53 |
| 4,616,631 | 10/1986 | Talahashi | 128/6 |
| 4,632,125 | 12/1986 | Webler et al. | 128/692 |
| 4,637,401 | 1/1987 | Johnston | 128/713 |

FOREIGN PATENT DOCUMENTS 0132215  1/1985  European Pat. Off. ............ 604/264

Primary Examiner—Max Hindenburg
Attorney, Agent, or Firm—Weingarten, Schurgin, Gagnebin & Hayes

[57] ABSTRACT

A composite catheter for in vivo fluid injection is provided in which a thin tube is located within the lumen of a conventional catheter. The thin tube has a small diameter inner passage for the in vivo injection of a fluid. The passage is accessible for fluid application at the exterior catheter end and passes through the catheter wall at a port in the lumen to the catheter exterior for fluid injection into the blood stream or elsewhere. A sensing device, such as a thermistor, is mounted on the catheter downstream of the port to measure changes in the properties of the fluid resulting from fluid injection for thermodilution applications. The space within the lumen insulates the fluid from the catheter environment and the small bore inner passage reduces resident fluid permitting small fluid injections that accommodate frequent injection measurements.

10 Claims, 1 Drawing Sheet

U.S. Patent  Apr. 4, 1989  4,817,624
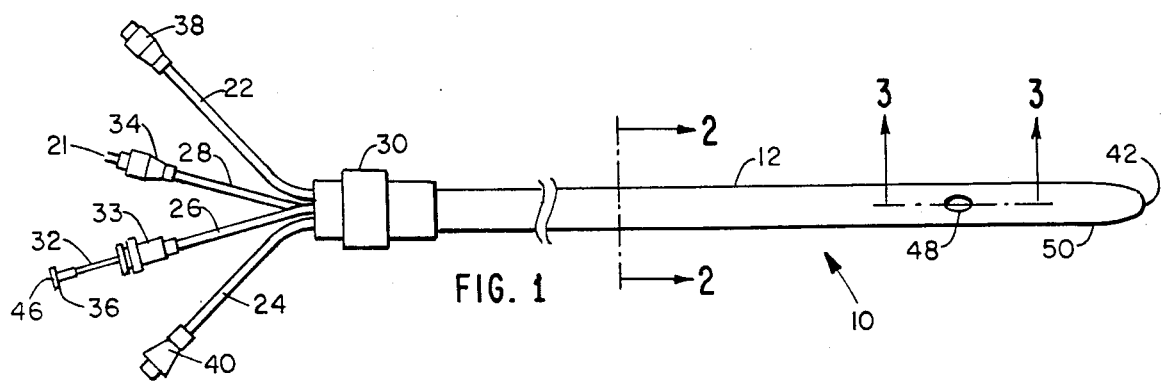
FIG. 1
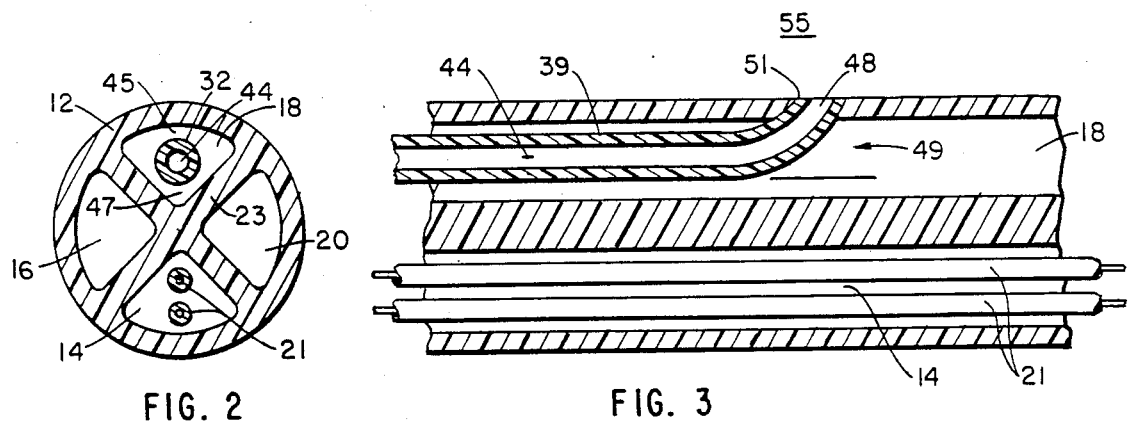
FIG. 2
FIG. 3
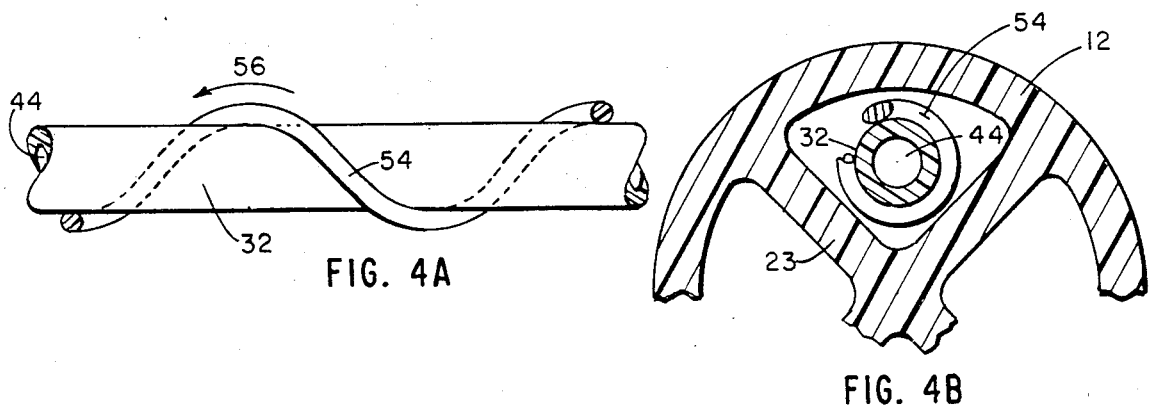
FIG. 4A
FIG. 4B
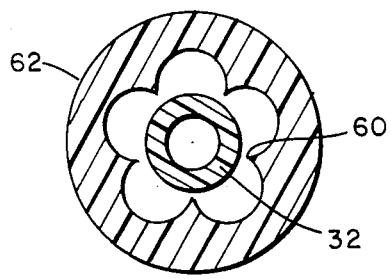
FIG. 5

4,817,624

MINI-BOLUS TECHNIQUE FOR THERMODILUTION CARDIAC OUTPUT MEASUREMENTS

FIELD OF THE INVENTION

This invention relates to catheters for medical applications, and more particularly to a structure for passing small volumes of injectate and the method of fabrication.

BACKGROUND OF THE INVENTION

The characteristics of a generally in accessible body through which a fluid flows can, in many cases, be determined by first adding to the fluid flow upstream of the body an injectate which modifies a property of the fluid, and then detecting changes in the modified property downstream. This technique is known in the field of medicine as thermodilution and generally involves injection of, for example, 10 cc's of cold saline through a catheter into a pulmonary artery. An incremental change in temperature produced by the cold saline is then detected downstream via a thermistor on the same catheter. The dead space in the injection lumen of a multi-lumen catheter is typically on the order of 1 cc, and accurate determinations require administration of volumes substantially larger the fluid resident in this dead space between injections. In addition, there is an uncertainty in the thermal loss involved in the injection process due in part to the transfer of heat between the lumen fluid and catheter environment, and in part to the warming of the fluid residing in the injection passageway between injections. To compensate for this loss, a large change in temperature, such as is only possible when a large volume of very cold saline is injected into the warmer bloodstream, is needed to swamp these small uncertainties. As a result, injectate volumes of approximately 10 cc's and temperatures of approximately 32° F. (0° C.) are generally required for acceptable accuracies.

While the injected fluid volume of the saline solution is innocuous for a single determination, it can become harmful to patients if repeated measurements are required. Many in the medical field have proposed automating the dilution measurement, so that it is repeated every few minutes with results of each measurement recorded. That sort of repetition, however, would require a substantial fluid administration in critically ill patients and require substantial refrigeration capability to cool the saline and maintain it at the required temperature. The former poses a health threat to the patient and the latter requires bulky, expensive equipment. These difficulties have frustrated the above-described attempts at automation.

BRIEF SUMMARY OF THE INVENTION

A catheter is constructed with a thin tube extending through a larger lumen in the catheter, thus making a tube within a tube. The inner tube is insulated from the catheter environment and thermal losses to the injectate fluid minimized. Internal dead space is also minimized, permiting a reduction in the amount of fluid injected for a given thermodilution or conductivity dilution application.

The inner tube is insulated by the lumen air space around it and this may be augmented by spacing means that separate the inner tube from the lumen wall. One end of the inner tube exits the catheter wall at a port located at a point typically positioned in the bloodstream. The other end of the inner tube, where the catheter exits, is an access for injecting an appropriate fluid, such as cold saline or conductivity dilutant.

Using the inner tube to carry the saline rather than a conventional lumen passage creates a much smaller dead space because of the smaller volume of the inner passage of the tube. This limits the volume of the resident fluid which is of uncertain temperature when the next injection occurs. The insulating space around the inner tube offers a low thermal loss to the injected fluid permitting a smaller volume to be more accurately used. Because of the smaller injection volume required, repeated determinations can be made without adverse effect on the patient, and refrigeration of the smaller quantity of injectate is more easily accomplished.

The inner tube can be fabricated of a material selected to be stiff to accommodate insertion and injection pressures without appreciably stiffening the catheter as a whole.

BRIEF DESCRIPTION OF THE DRAWING

These and other features of the subject invention are described in detail hereinafter in connection with the drawing of which:

FIG. 1 is a pictorial view of a four-lumen catheter;

FIG. 2 is a cross-sectional illustration along line II—II of FIG. 1, illustrating a possible catheter construction according to the present invention;

FIG. 3 is a cross-sectional illustration taken along line III—III of FIG. 1, illustrating an injectate port;

FIG. 4A is a perspective illustration of an inner tube thermally insulated with filament for use in the catheter of FIG. 1;

FIG. 4B is an enlarged cross-sectional illustration of the filament-wrapped inner tube within a catheter lumen;

FIG. 5 is a cross-section of a single lumen catheter illustrating an alternative means for insulatingly supporting a tube within a lumen.

DETAILED DESCRIPTION OF THE INVENTION

The present invention contemplates a catheter system utilizing an auxiliary small diameter inner tube that permits thermally accurate fluid injections of small fluid volumes.

FIGS. 1, 2 and 3 depict a four-lumen, thermodilution catheter assembly 10 with an outer tube 12 and lumens 14, 16, 18, and 20. Lumen walls 23 separate the lumens from each other inside the outer tube 12 over its length. The catheter tube can be of the Swan-Ganz type, such as Swan-Ganz flow-directed thermodilution catheter model 93A-131-7F marketed by Edwards Laboratories, Inc., Santa Ana, Calif. 92711. The four lumens 14, 16, 18, and 20 are coupled to respective tubes 22, 24, 26, and 28 via a coupling connector 30 as known in the art and illustrated in FIG. 1. A thermistor probe 50 is located on the inner tip of the catheter and its electrical leads 21 extend through the lumen 14 and its associated tube 28 terminates at a thermistor lead connector 34. Lumens 20 and 16, coupled to respective tubes 22 and 24, terminate at connectors 38 and 40. These lumens may be used to perform various functions related to thermodilution, such as balloon inflation.

The lumen 18 contains an inner tube 32. The lumen 18 terminates at a lumen connector 33, but the inner tube 32 extends through the lumen connector 33 to terminate at a further connector 36. Referring now to FIG. 2, the passage 44 of the inner tube 32 has a substantially smaller cross-sectional area than the passage 47 enclosed by lumen 18 through which the inner tube 32 passes. This construction leaves an insulating space 45 which extends over the length of the inner tube 32 between its wall 39, the opposing portions of lumen walls 23, and the opposing portion of the wall of outer tube 12. The insulating space 45 is typically air filled. When the catheter is bent or flexed during normal use, the opposing walls generally contact the inner wall at occasional points but do not contribute sufficient thermal conductivity to impair the insulating effect of space 45.

In one possible method of operation, distal end 42 of the catheter is inserted into a body. A thermal modifier, such as cold saline solution, is injected into the inner tube 32 at the connector end 46. The solution (injectate) travels in passage 44 of inner tube 32 typically under high pressure to speed the injection. Referring now to FIG. 3, the injectate exits the passage 44 and enters the bloodstream 55 at an injectate port 48 located in the exterior wall of the outer tube 12 near the distal end 42. The port is typically the same diameter as that of passage 44, on the order of 0.01 mm. At the injectate port 48, the walls 39 of the inner tube 32 are joined by conventional means, such as adhesive or thermal bonding, to the outer tube 12 at an angle designated by an arrow 49 to facilitate exit of the injectate. Edges 51 of the inner tube and the exterior of outer tube 12 form a smooth surface around injectate port 48, thereby avoiding any clotting effects. A means to measure the change in injectate properties, such as the thermistor 50 (FIG. 1), is located a sufficient distance away from the injectate port 48, usually at a point downstream.

By separating the cold injectate traveling in passage 44 from direct contact with the outer tube 12 which is warmed by the surrounding bloodstream 55, thermal losses conventionally sustained by the injectate are minimized. Dead space of the catheter is also reduced from 1 cc to less than or about 0.1 cc. With less thermal loss, and a smaller resident volume of passage 44, the amount of fluid required for thermodilution applications, such as cardiac output measurements, is reduced to one-tenth the usual amount (for example 1.0 cc).

The ultimate limitation on lower limit for the volume of injectate and inner diameter of tube 32 is the signal-to-noise ratio that the thermodilution measurement is capable of providing. That is, the signal provided by detection of injectate effect must be large enough relative to other contributions to provide useful data. Averaging several injections as described below will improve this ratio.

Because the invention reduces the amount of injectate per injection, many injections can be achieved, over time, for the same dosage of injectate as with a single injection in the prior art. This has several advantages. First, because the cardiac function detection is spread over time, the opportunity to detect an anomaly is greatly increased. Also the net signal-to-noise ratio achieved by several injections averaged is better than that of a single larger injection of the same dose. This results from the statistical manner in which error propagates by the root mean square effect in averages. This advantage can be realized even without the thermal insulation properties of the inner tube.

FIGS. 4A and 4B illustrate an alternative method for augmenting the thermal insulation of an injectate passage according to the present invention. A stand-off 54, such as a mono-filament line, surrounds the inner tube in spiral windings 56 and prevents inner tube 32 from any substantial contact with the catheter or lumen walls 12 or 33.

FIG. 5 illustrates another embodiment of the invention, wherein a single lumen catheter 62 has an irregular surface 60 on the lumen inner wall that acts to minimize thermal contact of the inner tube 32 with the catheter environment and thereby maintains the thermal insulation of inner tube 32.

In the several embodiments above, the outer tube can be constructed of either PVC or urethane, while the inner tube 32 is preferably formed of a stiffer material, such as Teflon R or a stronger grade of PVC or urethane, to allow for higher injection pressures. Increasing the stiffness of the inner tube, however, will not result in any significant change in overall catheter stiffness because of the small diameter of the inner tube. The greater rigidity of the inner tube facilitates inserting through the lumen.

The inner tube of the present invention can be used in other applications including combined thermal and conductivity modifiers for use in double indicator measurements, with warm injectates or radiological contrast materials requiring high injection pressures. Also, plural lumens may be instrumented with inner tubes according to the invention.

Having above indicated several preferred embodiments of the present invention, it will occur to those skilled in the art that modifications and alternatives can be practiced within the spirit of the invention. It is accordingly intended to define the scope of the invention only as indicated in the following claims.

What is claimed is:

1. A catheter for use in injection applications, comprising:
   a flexible outer tube having an outer wall, a first end, a second end, and a plurality of lumens, each lumen being bounded by lumen-defining walls and extending from the first end toward the second end of said outer tube; and
   a flexible inner tube having a wall defining an outer surface and an inner passage;
   said inner tube being located within one of the plurality of lumens and extending from the first end toward the second end of said outer tube and terminating in a port of said outer tube;
   said inner tube having a volume substantially less than the volume of the luemn in which it is located, so that said catheter possesses a low dead volume;
   said inner tube further being sufficiently smaller in cross-sectional area than the lumen in which it is located in leave space between the outer surface of the wall of said inner tube and the walls defining the lumen in which said inner tube is located;
   the combination of said outer tube, the wall of said inner tube, and the space about said inner tube thermally insulating the inner passage of said inner tube from the environment external to said catheter to a greater degree than said outer tube thermally insulates the catheter lumen which contains said inner tube, whereby said catheter permits multiple successive small-volume injections of fluid to be made in thermodilution applications without degradation of the temperature of each small-volume injection.

2. The catheter of claim 1 further comprising:
a thermistor probe having associated thermistor leads, said thermistor probe being located proximate to the second end of said outer tube and the associated thermistor leads being disposed within one of the plurality of lumens.

3. The catheter of claim 1 further comprising:
means for minimizing physical contact between the outer surface of said inner tube and the walls defining the lumen in which said inner tube is located.

4. The catheter of claim 3 wherein said means for minimizing physical contact comprises a plurality of projections from the walls defining the lumen in which said inner tube is located.

5. The catheter of claim 3 wherein said means for minimizing physical contact is a filament wound about said inner tube.

6. The catheter of claim 1 wherein the lumen in which said inner tube is located is air-filled.

7. The catheter of claim 1 wherein the inner passage of said inner tube has a volume of less than 0.1 cubic centimeters.

8. A catheter for use in thermodilution injection applications comprising:
a flexible tube having an outer surface;
said flexible tube having at least one interior region remote from said outer surface and containing an inner passage;
said flexible tube having a distal end adapted for injection of a fluid from said inner passage of said flexible tube into a body vessel of the vasculature system;
said flexible tube outer surface diameter being sufficiently small to pass through said body vessel;
said flexible tube having a proximal end adapted to receive an injectate fluid into said inner passage;
said inner passage of said flexible tube having a dead space of less than or approximately 0.1 cc; and
heat transfer impedance means between said interior region and said outer surface for limiting thermal loss from said inner passage, whereby a temperature of injectate in said inner passage is maintained during thermodilution injection.

9. The catheter of claim 8 wherein said reduction in total injectate volume is approximately an order of magnitude or more.

10. The catheter of claim 8 wherein said means for limiting thermal loss includes means for providing an immediate environment for said tube having a low thermal mass.

* * * * *

UNITED STATES PATENT AND TRADEMARK OFFICE
CERTIFICATE OF CORRECTION

PATENT NO. : 4,817,624
DATED : April 4, 1989
INVENTOR(S) : Ronald S. Newbower

It is certified that error appears in the above-identified patent and that said Letters Patent is hereby corrected as shown below:

Column 1, line 13, "in accessible" should read --inaccessible--

Column 1, line 27, "larger the" should read --larger than the--

Column 2, line 29, re: Figure 1, "II-II" should read --2-2--.

Column 2, line 32, re: Figure 1, "III-III" should read --3-3--.

Column 4, line 7, "or 33." should read --or 23.--.

Column 4, line 57, "in leave" should read --to leave--.

Signed and Sealed this

Nineteenth Day of March, 1991

Attest:

HARRY F. MANBECK, JR.

*Attesting Officer*  *Commissioner of Patents and Trademarks*